(12) United States Patent
Berndt et al.

(10) Patent No.: US 6,933,407 B2
(45) Date of Patent: Aug. 23, 2005

(54) METHOD FOR PRODUCING METHACRYLIC ACID FROM ISOBUTANE

(75) Inventors: Silke Berndt, Mannheim (DE); Klaus Joachim Müller-Engel, Stutensee (DE); Götz-Peter Schindler, Mannheim (DE); Frank Rosowski, Mannheim (DE); Jochen Petzoldt, Mannheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/480,651

(22) PCT Filed: Jun. 28, 2002

(86) PCT No.: PCT/EP02/07175
§ 371 (c)(1),
(2), (4) Date: Dec. 29, 2003

(87) PCT Pub. No.: WO03/002493
PCT Pub. Date: Jan. 9, 2003

(65) Prior Publication Data
US 2004/0242925 A1 Dec. 2, 2004

(30) Foreign Application Priority Data

| Jun. 29, 2001 | (DE) | 101 31 297 |
|---|---|---|
| Mar. 13, 2002 | (DE) | 102 11 275 |
| May 2, 2002 | (DE) | 102 19 685 |

(51) Int. Cl.$^7$ ................................................ C07C 51/16
(52) U.S. Cl. ...................... 562/549; 562/542; 562/543; 562/523
(58) Field of Search ................................ 562/512, 523, 562/531, 532, 598

(56) References Cited

U.S. PATENT DOCUMENTS 4,535,188 A * 8/1985 Khoobiar .................... 568/479

FOREIGN PATENT DOCUMENTS

| DE | 25 47 536 | 4/1976 |
|---|---|---|
| DE | 33 13 573 | 10/1983 |

* cited by examiner

Primary Examiner—Johann Richter
Assistant Examiner—Karl Puttlitz
(74) Attorney, Agent, or Firm—Oblon, Spivak, McClelland, Maier & Neustadt, P.C.

(57) ABSTRACT

A process prepares methacrylic acid from isobutane by subjecting isobutane to a partial catalytic dehydrogenation in the gas phase and charging an oxidation zone with the isobutenic product gas mixture after the components other than isobutane and isobutene have been substantially removed from the product gas mixture. The oxygen required to charge the oxidation zone is introduced accompanied by nitrogen.

11 Claims, No Drawings

METHOD FOR PRODUCING METHACRYLIC ACID FROM ISOBUTANE

BACKGROUND OF THE INVENTION

1. Field of the Invention

The present invention relates to a process for preparing methacrylic acid from isobutane by A) subjecting the isobutane in a reaction zone A to a partial selective heterogeneously catalyzed dehydrogenation in the gas phase to form a product mixture A which comprises isobutene and unconverted isobutane, B) using the isobutane- and isobutene-containing product gas mixture A to charge a reaction zone B and subjecting the isobutene in reaction zone B to a selective heterogeneously catalyzed partial oxidation in the gas phase using molecular oxygen to form a methacrolein-containing product gas mixture B with the proviso that the molar conversion of isobutene is $\geq 95$ mol % and C) using the methacrolein-containing product gas mixture B without preceding removal of components contained therein to charge a reaction zone C and subjecting the methacrolein in reaction zone C to a selective heterogeneously catalyzed partial oxidation using molecular oxygen in the gas phase to form a methacrylic acid-containing product gas mixture C.

2. Discussion of the Background

Methacrylic acid is an important staple chemical which is used as such and/or in the form of its methyl ester for preparing polymers which are used, for example, finely dispersed in an aqueous medium as a binder.

DE-A 3313573 discloses a process for preparing methacrylic acid from isobutane as described at the outset. A procedure considered particularly advantageous by DE-A 3313573 involves using the product gas mixture A without preceding removal of components contained therein for charging reaction zone B and using pure oxygen as the source for the molecular oxygen required in reaction zone B.

However, disadvantages of such a procedure are that on the one hand the selectivity of methacrylic acid formation per se and on the other hand the extent of formation of the by-produced isobutyraldehyde and isobutyric acid, which are particularly undesirable even in very small quantities since they are difficult to remove from the target product and are particularly troublesome in subsequent uses, is not completely satisfactory.

SUMMARY OF THE INVENTION

It is an object of the present invention to provide a process for preparing methacrylic acid from isobutane as described at the outset which only has the disadvantages described to a reduced extent.

DETAILED DESCRIPTION OF THE INVENTION

We have found that this object is achieved by a process for preparing methacrylic acid from isobutane by A) subjecting the isobutane in a reaction zone A to a partial selective heterogeneously catalyzed dehydrogenation in the gas phase to form a product mixture A which comprises isobutene and unconverted isobutane, B) using the isobutane- and isobutene-containing product gas mixture A to charge a reaction zone B and subjecting the isobutene in reaction zone B to a selective heterogeneously catalyzed partial oxidation using molecular oxygen in the gas phase to form a methacrolein-containing product gas mixture B with the proviso that the molar conversion of isobutene is $\geq 95$ mol % and C) using the methacrolein-containing product gas mixture B without preceding removal of components contained therein to charge a reaction zone C and subjecting the methacrolein in reaction zone C to a selective heterogeneously catalyzed partial oxidation using molecular oxygen in the gas phase to form a methacrylic acid-containing product gas mixture C, which comprises removing at least 80 mol % of the components other than isobutane and isobutene from the isobutane- and isobutene-containing product gas mixture A before it is used to charge reaction zone B, and introducing the molecular oxygen required in reaction zone B to reaction zone B accompanied by molecular nitrogen in a molar ratio R of molecular oxygen to molecular nitrogen of from 1:1 to 1:10.

In other words, according to the invention, R may be 1:2, or 1:3, or 1:4, or 1:5, or 1:6, or 1:7, or 1:8, or 1:9, or 1:10. An advantageous ratio R is in the range from 1:2 to 1:5 or in the range from 1:3 to 1:5, or from 1:3.5 to 1:4.5. In the process according to the invention, the abovementioned accompaniment of the molecular oxygen by molecular nitrogen is advantageously realized in such a manner that the molecular oxygen is introduced into reaction zone B as a component of a gas which already comprises the molecular oxygen and molecular nitrogen in an abovementioned ratio R or consists only of molecular oxygen and molecular nitrogen in such a ratio R. In the process according to the invention, preference is given to at least partially, more preferably predominantly or exclusively, using air as the source for the molecular oxygen required in reaction zone B. However, it is also possible to introduce to reaction zone B, for example, air and additionally molecular oxygen or air and additional molecular nitrogen or air and additionally a mixture of molecular nitrogen and molecular oxygen which comprises the two gas components in a ratio other than that in air. It is essential to the invention only that the ratio R be maintained overall. According to the invention, molecular oxygen and molecular nitrogen could also be introduced spatially separated to the reaction zone B.

In other words, while DE-A 3313573 teaches the selective heterogeneously catalyzed partial oxidation of isobutene in reaction zone B in a reaction gas mixture which comprises in particular iso-butene, isobutane and molecular oxygen, the reaction gas mixture in reaction zone B in the process according to the invention necessarily contains isobutene, isobutane, molecular oxygen and molecular nitrogen. The additional presence of the latter in the process according to the invention surprisingly ensures a reduction in the undesired conversion of isobutane to undesired by-product.

A further feature essential to the invention consists in the removal of at least 80 mol % of the components other than isobutane and isobutene from the isobutane- and isobutene-containing product gas mixture A before it is used to charge reaction zone B. The molar reference basis is the sum of the molar amounts of the different individual components contained in the product gas mixture B. According to the invention, the abovementioned removal does not have to be homogeneous over the different components. Rather, it may capture individual components quantitatively and others only partially. Only the sum total has to achieve the abovementioned percentage of 80 mol %. According to the invention, preference is given to removing at least 85 mol %, more preferably at least 90 mol %, even more preferably at least 95 mol %, even better 97 mol % and at best at least 99 mol % or 100 mol %, of the components other than isobutane and isobutene from the product gas mixture A before it is used to charge reaction zone B.

It will be appreciated that the charging gas mixture (=the mixture of all gas streams introduced into the reaction zone) of reaction zone B in the procedure according to the invention comprises, in addition to the components already mentioned, other components, for example, CO, $CO_2$, $H_2O$, noble gases such as He and/or Ar, hydrogen, methane, ethylene, ethane, butanes, butenes, butynes, pentanes, propyne, allenes, propane, propylene, acrolein and/or methacrolein.

According to the invention, the molecular nitrogen content of the charging gas mixture of reaction zone B, based on the amount of isobutene contained in this charging gas mixture, should not be less than 500 mol %. In other words, the molecular nitrogen content of the charging gas mixture of reaction zone B in the process according to the invention, based on the amount of isobutene present, can be at least 500 mol %, or at least 600 mol %, or at least 700 mol %. However, the ratio of the molar quantity of molecular nitrogen contained in the charging gas mixture of reaction zone B to the amount of isobutene contained in the charging gas mixture of reaction zone B according to the invention will normally be $\leq 20:1$, frequently $\leq 12:1$.

The molar ratio of the amount of molecular nitrogen contained in the charging gas mixture of reaction zone B to the amount of isobutane in the charging gas mixture of reaction zone B in the process according to the invention will generally not be less than 1:1. Normally, this ratio will also not be above 16:1.

In other words, the molar ratio of the amount of molecular nitrogen contained in the charging gas mixture of reaction zone B to the amount of isobutane contained in the charging mixture for reaction zone B can, according to the invention, be from 1:1 to 16:1, or from 2:1 to 10:1, or from 2:1 to 4:1.

Frequently, the composition of the charging gas mixture of reaction zone B in the process according to the invention will be selected in such a manner that the following molar ratios are fulfilled:

iso-butane:iso-butene:$N_2$:$O_2$:$H_2O$:$H_2$:others=
10–40:4–8:20–70:5–20:0–20:0–5:0–5.

According to the invention, the abovementioned molar ratios advantageously= 15–25:4–8:40–60:10–15:5–15:0–1:0.1–3. Frequently, they will be 20:6:50:12:10:0:2.

An essential feature of the procedure according to the invention is that, in contrast to the case of a homogeneously and/or heterogeneously catalyzed partial oxydehydrogenation of isobutane, molecular hydrogen is formed at least intermediately in reaction zone A, which is why the product gas mixture A generally comprises molecular hydrogen. Furthermore, the catalytic dehydrogenation in reaction zone A is endothermic without additional measures, while a catalytic oxydehydrogenation is exothermic.

According to the invention, before the product gas mixture A is used to charge reaction zone B, at least 80 mol %, preferably at least 85 mol %, more preferably at least 90 mol %, even more preferably at least 95 mol %, or at least 97 mol %, or at least 99 mol %, and frequently the entire amount, of the molecular hydrogen contained therein will be removed.

In general, the molar ratio of isobutene contained in the product gas mixture A to the molecular hydrogen contained in the product gas mixture A in the process according to the invention will be $\leq 10$, customarily $\leq 5$, frequently $\leq 3$ and often $\leq 2$.

Normally, the reciprocal of the abovementioned ratio will not exceed 2. In other words, the molar ratio of isobutene contained in the product gas mixture A to molecular hydrogen contained in the product gas mixture A in the process according to the invention will customarily be $\geq 0.5$, usually $\geq 0.8$, and in many cases $\geq 1.2$ or 1.5.

In contrast, the molar ratio of molecular hydrogen contained in the charging gas mixture of reaction zone B (i.e. in charging gas mixture B) to the isobutene contained in the charging gas mixture B in the process according to the invention will generally be $\leq 1:10$, customarily $\leq 1:50$, often $\leq 1:100$.

In addition to molecular hydrogen, components other than isobutane and isobutene contained in product gas mixture A are gases from the group consisting of $N_2$, CO, $CO_2$, $H_2O$, methane, ethane, ethylene, propane, propylene and also possibly $O_2$ and others.

It will be appreciated that in the process according to the invention, the abovementioned components will be removed to a substantial extent from the isobutane and isobutene contained in the product gas mixture A before it is used to charge reaction zone B (for example, at least 80 mol %, or at least 85 mol %, or at least 90 mol %, or at least 95 mol %, or at least 97 mol %, or at least 99 mol %, thereof) or completely from the isobutane and isobutene contained in the product gas mixture A, generally in combination, i.e. normally together with the molecular hydrogen contained in the product gas mixture A. However, such combined removal is not vital according to the invention. Rather, more of one component contained in the product gas mixture A and less of another component contained in the product gas mixture A may be removed according to the invention. However, according to the invention, at least a portion of all of the components other than isobutane and isobutene will preferably be removed from product gas mixture A before it is used to charge reaction zone B.

In order to achieve interesting conversions in reaction zone A in the partial heterogeneously catalyzed dehydrogenation to be carried out according to the invention, based on a single pass, operation generally has to be effected at relatively high reaction temperatures (typically these reaction temperatures are from 300 to 70° C.). Since the dehydrogenation (cleavage of C—H) is kinetically disadvantaged compared to cracking (cleavage of C—C), it is effected on selective catalysts. For every isobutene molecule formed, a hydrogen molecule is generally by-produced. As a consequence of the selective catalysts which are customarily configured in such a manner that they display significant dehydrogenation (at isobutane gas hourly space velocities of, for example, 1000 $h^{-1}$ (1 at STP/1 of cat. h), the isobutene yield is generally at least 30% in a single pass (based on isobutane used)) with the exclusion of oxygen at the abovementioned temperatures (for example at 600° C.), and by-products such as methane, ethylene, propane, propene and ethane are only formed in insignificant amounts.

Since the dehydrogenation reaction proceeds with decreasing volume, the conversion may be increased by reducing the partial pressure of the products. This can be achieved in a simple manner, for example, by dehydrogenating at reduced pressure and/or by admixing in substantially inert diluent gases, for example steam, which is normally an inert gas for the dehydrogenation reaction. Dilution with steam generally has the further advantage of reduced coking of the catalyst used, since the steam reacts with coke formed by the principle of coal gasification. Also, steam may be used as a diluent gas in the subsequent oxidation stage B. Steam can also be readily removed partially or completely from the product gas mixture A of the process A according to the invention (for example by condensation) which opens up the possibility of increasing the proportion in reaction zone B of the diluent gas $N_2$, whose use is essential to the invention, in the further use of the product gas mixture A' obtainable in this way. According to the invention, it is entirely possible to use the entirety or else only a portion of the molecular nitrogen to be used in reaction zone B according to the invention, also for dilution in reaction zone A. Examples of further diluents for reaction zone A include CO, $CO_2$ and noble gases such as He, Ne and Ar. However, operation in reaction zone A may in principle also be effected without diluents; i.e. the charging gas mixture of reaction zone A may consist only of isobutane or only of isobutane and molecular oxygen. All of the diluents mentioned may be used in reaction zone A either alone or in the form of highly varying mixtures. According to the invention, it is advantageous that the diluents suitable for reaction zone A are generally also diluents suitable for reaction zone B, so that their quantitative removal from the product gas mixture A is not indispensable to the invention. In general, preference is given to diluents which behave inertly (i.e. less than 5 mol %, preferably less than 3 mol % and even better less than 1 mol % are chemically altered) in each reaction zone. In principle, all dehydrogenation catalysts known from the prior art are suitable for stage A according to the invention. They can be roughly divided into two groups, i.e. those of oxidic nature (for example chromium oxide and/or aluminum oxide) and those which consist of at least one generally comparatively precious metal (for example platinum) deposited on at least one generally oxidic support.

Dehydrogenation catalysts which may be used for stage A according to the invention are, inter alia, all of those recommended by DE-A 10060099 (the example), WO 99/46039, U.S. Pat. No. 4,788,371, EP-A 705 136, WO 99/29420, U.S. Pat. No. 5,220,091, U.S. Pat. No. 5,430,220, U.S. Pat. No. 5,877,369, DE-A 10047642, EP-A 117 146, DE-A 19 937 106, DE-A 19 937 105, DE-A 10 211 275 and also DE-A 19 937 107. In particular, all the dehydrogenation process variants mentioned in this document as being suitable for reaction zone A according to the invention may be carried out using the catalyst according to Example 1, and also according to Example 2, and also according to Example 3, and also according to Example 4 of DE-A 19 937 107.

These are dehydrogenation catalysts which comprise from 10 to 99.9% by weight of zirconium dioxide, from 0 to 60% by weight of aluminum oxide, silicon dioxide and/or titanium dioxide and from 0.1 to 10% by weight of at least one element of the first or second main group, of an element of the third transition group, of an element of the eighth transition group of the periodic table, of lanthanum and/or of tin, with the proviso that the sum total of the percentages by weight is 100% by weight.

The at least one catalyst bed (for example fluidized bed, moving bed or fixed bed) required for the purposes of the present invention may contain the dehydrogenation catalyst in differing geometries. Examples of useful geometries for the process according to the invention include shapes such as spall, tablets, monoliths, spheres or extrudates (rods, wagonwheels, stars, rings).

In the case of extrudates, the length is advantageously from 2 to 15 mm, frequently from 2 to 10 mm, in many cases from 6 to 10 mm, and the diameter of the extrudate cross section is advantageously from 1 to 5 mm, frequently from 1 to 3 mm. In the case of rings, the wall thickness is advantageously from 0.3 to 2.5 mm, and the length is from 2 to 15 mm, frequently from 5 to 15 mm, and the diameter of the cross section from 3 to 10 mm. A suitable shaping process is disclosed, for example, by DE-A 10047642 and also DE-A 19937107. The process is based on the fact that oxidic support materials admixed with concentrated mineral acid (for example concentrated nitric acid) can be comparatively efficiently kneaded and can be converted by means of an extruder or an extrudate press to an appropriate shaped body.

The shaped bodies are then dried and calcined and then salt solutions are poured over them in a suitable sequence. Finally, they are again dried and calcined.

The reaction zone A relevant for the process according to the invention may in principle be realized in all reactor types known from the prior art for heterogeneously catalyzed partial dehydrogenations of hydrocarbons in the gas phase over fixed-bed catalysts.

Typical reaction temperatures are from 200 to 800° C., or from 400 to 650° C. The working pressure is typically in the range from 0.5 to 10 bar. Typical gas hourly space velocities of reaction gas are from 300 to 16 000 $h^{-1}$.

In principle, all reactor types and process variants known from the prior art may be used to embody reaction zone A of the process according to the invention. Descriptions of such process variants are contained in, for example, all prior art documents mentioned in relation to the dehydrogenation catalysts.

A comparatively comprehensive description of dehydrogenation processes suitable according to the invention is also contained in "Catalytica® Studies Division, Oxidative Dehydrogenation and Alternative Dehydrogenation Processes, Study Number 4192 OD, 1993, 430 Ferguson Drive, Mountain View, Calif., 94043-5272 U.S.A.".

A characteristic feature of the partial heterogeneously catalyzed dehydrogenation of isobutane is that it is endothermic. In other words, the heat (energy) necessary to achieve the required reaction temperature has to be supplied either in advance to the reaction gas and/or in the course of the catalytic dehydrogenation.

Also, owing to the high reaction temperatures required, it is typical of heterogeneously catalyzed dehydrogenations of isobutane that small amounts of high-boiling, high molecular weight organic compounds, up to and including carbon, are formed which deposit on the catalyst surface and thus deactivate it. In order to minimize this disadvantageous side effect, it is possible, as already mentioned, to dilute with steam the isobutane to be passed over the catalyst surface at elevated temperature for catalytic dehydrogenation. Under the resulting conditions, depositing carbon is partially or completely eliminated by the principle of coal gasification.

Another possible way of removing deposited carbon compounds consists in passing an oxygen-containing gas through the dehydrogenation catalyst at elevated temperature from time to time and effectively burning off the deposited carbon. However, it is also possible to suppress carbon deposit formation by adding molecular hydrogen to the isobutane to be catalytically dehydrogenated before it is passed over the dehydrogenation catalyst at elevated temperature.

It will be appreciated that the possibility also exists of adding a mixture of steam and molecular hydrogen to the isobutane to be catalytically dehydrogenated. Addition of molecular hydrogen to the catalytic dehydrogenation of isobutane also reduces the undesired formation of by-produced allene, acetylene and other carbon precursors.

In the majority of processes known for heterogeneously catalyzed partial dehydrogenation of hydrocarbons such as isobutane to be dehydrogenated, the heat of dehydrogenation is generated outside the reactor and supplied to the reaction gas from outside. However, this requires complicated reactor and process concepts and leads, particularly at high conversions, to steep temperature gradients in the reactor with the general disadvantage of increased by-product formation.

Alternatively, the heat of dehydrogenation may also be generated directly in the reaction gas itself by adding molecular oxygen and exothermically combusting hydrogen formed either in the dehydrogenation or supplied additionally to give steam. To this end, a molecular oxygen-containing gas and optionally hydrogen are added to the reaction gas before and/or after entrance into the reaction zone containing the dehydrogenation catalyst. Either the dehydrogenation catalyst itself (this applies to most dehydrogenation catalysts) and/or any additionally installed oxidation catalysts generally ease the desired hydrogen oxidation (cf. DE-A 10028582). In favorable cases, heat of reaction released in this manner by means of hydrogen combustion allows indirect reactor heating to be completely dispensed with and accordingly comparatively simple process concepts and also limited temperature gradients in the reactor even at high conversions.

In the above procedure, the use of external molecular hydrogen may, for example, be avoided when the process principle of DE-A 10 211 275 is applied.

According to this process principle, a reaction gas containing the at least one hydrocarbon to be dehydrogenated (isobutane in this case) is continuously introduced into the catalytic dehydrogenation zone (reaction zone A in this case). In the catalytic dehydrogenation zone, the reaction gas is passed over at least one fixed catalyst bed where molecular hydrogen and some of at least one dehydrogenated hydrocarbon (isobutene in this case) are formed by catalytic dehydrogenation. Before and/or after entry into the catalytic dehydrogenation zone, at least one molecular oxygen-containing gas which at least partially oxidizes the molecular hydrogen contained in the reaction gas in the catalytic dehydrogenation zone to give steam is added to the reaction gas. A product gas mixture is then withdrawn from the catalytic dehydrogenation zone which comprises molecular hydrogen, steam, the at least one dehydrogenated hydrocarbon and the at least one hydrocarbon to be dehydrogenated, divided into two portions of identical composition and one of the two portions is returned to the catalytic dehydrogenation zone (cycle gas) as the source for molecular hydrogen.

In the process according to the invention, the other portion would be withdrawn as product gas mixture A and, according to the removal of the invention, introduced into reaction zone B.

It will be appreciated that reaction zone A in the process according to the invention may also be configured in such a manner that there is a further fixed catalyst bed downstream of the dehydrogenation catalyst fixed bed in the flow direction of the reaction gas where molecular hydrogen contained in the reaction gas is at least partially combusted to steam by selective heterogeneous catalysis so that the product gas mixture A in the process according to the invention may be substantially or completely free of hydrogen. Catalysts suitable for this purpose are disclosed by, for example, U.S. Pat. No. 4,788,371, U.S. Pat. No. 4,886,928, U.S. Pat. No. 5,430,209, U.S. Pat. No. 55,530,171, U.S. Pat. No. 5,527,979, EP-A 832056 and U.S. Pat. No. 5,563,314.

A useful reactor form for reaction zone A according to the invention is the fixed bed tubular or tube bundle reactor. In other words, the dehydrogenation catalyst and any specific hydrogen oxidation catalyst, as disclosed, for example, in the documents U.S. Pat. Nos. 4,788,372, 4,886,928, 5,430,209, 5,550,171, 5,527,979, 5,563,314 and EP-A 832 056 is disposed in a reaction tube or in a bundle of reaction tubes as a fixed bed. The reaction tubes are customarily indirectly heated by combusting a gas, for example a hydrocarbon such as methane, in the space surrounding the reaction tubes. It is advantageous to apply this indirect form of heating only to the first 20 to 30% of the fixed bed and to heat the remaining bed length to the required reaction temperature using the radiative heat released in the combustion. Indirect heating of the reaction gas may be combined advantageously with direct heating by combustion with molecular oxygen in the reaction gas. In this manner, a virtually isothermal reaction is achievable in a comparatively simple form.

Suitable reaction tube internal diameters are from about 10 to 15 cm. A typical dehydrogenation tube bundle reactor comprises from 300 to 1000 reaction tubes. The temperature in the reaction tube interiors is in the range from 300 to 700° C., preferably in the range from 400 to 700° C. The working pressure is customarily in the range from 0.5 to 8 bar, frequently from 1 to 2 bar or else from 3 to 8 bar. Advantageously, the reaction gas is introduced into the tubular reactor preheated to the reaction temperature. In general, the product gas mixture leaves the reaction tube at a (higher or lower) temperature other than the entrance temperature (cf. also U.S. Pat. Nos. 4,902,849,4,996,387 and 5,389,342). For the purposes of the abovementioned procedure, it is advantageous to use oxidic dehydrogenation catalysts based on chromium oxide and/or aluminum oxide. Frequently, no diluent gas will be used, and instead substantially pure isobutane will be used as the starting reaction gas. The dehydrogenation catalyst is usually also used undiluted. Typical isobutane gas hourly space velocities are from 500 to 2000 h$^{-1}$ (=1 at STP/l of catalyst h).

On the industrial scale, about three tube bundle reactors would be operated in parallel, two of which would generally be carrying out dehydrogenation, while one of the reactors regenerates the catalyst charge.

It will be appreciated that reaction zone A according to the invention can also be configured within a moving bed. For example, the moving catalyst bed may be accommodated in a radial flow reactor. In this, the catalyst moves gradually from top to bottom while the reaction gas mixture flows radially. This procedure is used, for example, in the UOP Oleflex dehydrogenation process. Since the reactors in this process are operated virtually adiabatically, it is advantageous to operate more than one reactor in series (typically up to four). This allows excessively high differences in the temperatures of the reaction gas mixture at the reactor entrance and reactor exit to be avoided (in the adiabatic mode, the starting reaction gas mixture functions as a heat carrier on whose heat content the reaction temperature is dependent) and, despite this, attractive overall conversions to be achieved.

When the catalyst bed has left the moving bed reactor, it is regenerated and then reused. An example of a dehydrogenation catalyst for this process is a spherical dehydrogenation catalyst which consists substantially of platinum on a spherical aluminum oxide support. In order to avoid premature catalyst aging, hydrogen is advantageously added to the isobutane to be dehydrogenated. The working pressure is typically from 1 to 5 bar. The hydrogen to isobutane (molar) ratio is advantageously from 0.1 to 1. The reaction temperatures are preferably from 550 to 650° C. and the gas hourly space velocity of reaction gas mixture is from about 200 to 1000 h$^{-1}$. The catalyst charge may also consist of a mixture of dehydrogenation and H$_2$ oxidation catalysts, as recommended by EP-A 832 056.

In the fixed bed processes described, the catalyst geometry may likewise be spherical, or else cylindrical (hollow or solid).

A further process variant for reaction zone A according to the invention is described by Proceedings De Witt, Petrochem. Review, Houston, Tex. 1992 a, N1, which contemplates the possibility of a heterogeneously catalyzed dehydrogenation in a fluidized bed without diluting the isobutane.

This variant advantageously involves operating two fluidized beds in parallel, of which one is generally in the process of regeneration. The active composition used is chromium oxide on aluminum oxide. The working pressure is typically from 1 to 1.5 bar and the dehydrogenation temperature is generally from 550 to 600° C. The heat required for the dehydrogenation is introduced into the reaction system by preheating the dehydrogenation catalyst to the reaction temperature. The working pressure is regularly from 1 to 2 bar and the reaction temperature typically from 550 to 600° C. The above dehydrogenation method is also disclosed in the literature as the Snamprogetti-Yarsintez process.

As an alternative to the above-described procedures, reaction zone A according to the invention may also be realized according to a process developed by ABB Lummus Crest (cf. Proceedings De Witt, Petrochem. Review, Houston, Tex., 1992, P1).

Common to the heterogeneously catalyzed dehydrogenation processes for isobutane described hitherto is that they are operated at isobutane conversions of >30 mol % (in general ≦70 mol %) (based on single reactor pass).

An advantage of the present invention is that it is sufficient for the process according to the invention for an isobutane conversion of from ≧5 mol % to ≦30 mol % or ≦25 mol % to be achieved in reaction zone A. In other words, reaction zone A may also be operated at isobutane conversions of from 10 to 30 mol % according to the invention (the conversions relate to single reactor pass). Among other factors, this results from the dilution with molecular nitrogen of the remaining amount of unconverted isobutane in the downstream reaction zone B, which reduces the by-production of isobutyraldehyde and/or isobutyric acid.

The nitrogen has substantially the same effect in reaction zone C.

To realize the abovementioned isobutane conversions, it is advantageous to carry out the isobutane dehydrogenation according to the invention in reaction zone A at a working pressure of from 0.3 to 3 bar. It is further advantageous to dilute the isobutane to be dehydrogenated with steam. On the one hand, the heat capacity of the water allows the endothermic effect of the dehydrogenation to be partially compensated for and, on the other hand, dilution with steam reduces the reactant and product partial pressures, which has an advantageous effect on the dehydrogenation equilibrium location. In addition, the concomitant use of steam, as already mentioned, has an advantageous effect on the onstream time of the dehydrogenation catalyst. If required, molecular hydrogen may also be added as a further component. The molar ratio of molecular hydrogen to isobutane is generally ≦5. The molar ratio of steam to isobutane in the reaction zone A variant with comparatively low isobutane conversion may accordingly be from ≧0 to 30, conveniently from 0.1 to 2 and advantageously from 0.5 to 1. It has also proven advantageous for a procedure with low isobutane conversion that only a comparatively low heat quantity is consumed in single reactor pass of the reaction gas and comparatively low temperatures are sufficient to achieve the conversion in single reactor pass.

According to the invention, it is therefore advantageous in the reaction zone A variant with comparatively low isobutane conversion to carry out the isobutane dehydrogenation (quasi) adiabatically. In other words, the starting reaction gas mixture will generally be heated to a temperature of from 500 to 700° C. (for example by direct firing of the wall surrounding it in a heater), or to from 550 to 650° C. Normally, a single adiabatic pass through a catalyst bed will then be sufficient to achieve the desired conversion, and the reaction gas mixture will cool by from about 30° C. to 200° C. (depending on the conversion). The presence of steam as a heat carrier is also advantageous from the point of view of an adiabatic method. The relatively low reaction temperature allows relatively long onstream times of the catalyst bed used.

In principle, the reaction zone A variant according to the invention having comparatively low isobutane conversion, whether performed adiabatically or isothermally, may also be carried out either in a fixed bed reactor or else in a moving bed or fluidized bed reactor.

Remarkably, a single shaft furnace reactor as the fixed bed reactor, through which the reaction gas mixture flows axially and/or radially, is sufficient to realize this variant, particularly in adiabatic operation.

In the simplest case, this reactor is a single reaction tube whose internal diameter is from 0.1 to 10 m, possibly also from 0.5 to 5 m, where the fixed catalyst bed is mounted on a supporting device (for example a grid). The reaction tube charged with catalyst, which may be heat-insulated in adiabatic operation, is flowed through axially by the hot, isobutane-containing reaction gas. The catalyst geometry may be either spherical, extruded or annular. However, the catalyst may advantageously also be used in the abovementioned case in the form of spall. To realize radial flow of the isobutane-containing reaction gas, the reactor may consist, for example, of two concentric cylindrical grids disposed in a jacket and the catalyst bed may be arranged in the annular gap between them. In the adiabatic case, the jacket would in turn be thermally insulated.

Useful catalyst charges for the reaction zone A variant according to the invention with comparatively low isobutane conversion in a single pass are in particular the catalysts disclosed by DE-A 19 937 107, above all those disclosed by way of example.

After a relatively long operation time, the abovementioned catalysts can be regenerated, for example, in a simple manner by initially passing nitrogen, and/or steam-diluted air over the catalyst bed in first regeneration stages at a temperature of from 300 to 900° C., frequently from 400 to 800° C., often from 500 to 700° C. The gas hourly space velocity of regeneration gas may be, for example, from 50 to 10 000 h$^{-1}$ and the oxygen content of the regeneration gas may be from 0.5 to 20% by volume.

In the further downstream regeneration stages, air may be used as the regeneration gas under otherwise identical regeneration conditions. It has proven advantageous from an application point of view to purge the catalyst before regeneration with inert gas (for example N$_2$).

It is then generally recommended to regenerate further with pure molecular hydrogen or with molecular hydrogen diluted with inert gas (the hydrogen content should be ≧1% by volume) under otherwise identical conditions.

Frequently, it is advantageous to carry out the regeneration procedure twice or more in succession.

The reaction zone A variant according to the invention with comparatively low isobutane conversion (≦30 mol %) may in all cases be operated at the same gas hourly space velocities (relating both to the overall reaction gas and to the isobutane contained therein) as the variants with high isobutane conversion (>30 mol %). This gas hourly space velocity of reaction gas may be, for example, from 100 to 10 000 $h^{-1}$, frequently from 100 to 3000 $h^{-1}$, i.e. in many cases from 100 to 2000 $h^{-1}$.

In a particularly elegant manner, the reaction zone A variant according to the invention with comparatively low isobutane conversion can be realized in a tray reactor.

This comprises more than one catalyst bed catalyzing the dehydrogenation in spatial succession. The catalyst bed number may be from 1 to 20, advantageously from 2 to 8 but also from 4 to 6. The catalyst beds are preferably arranged in radial or axial succession. From an application point of view, it is advantageous to used the fixed catalyst bed type in such a tray reactor.

In the simplest case, the fixed catalyst beds in a shaft furnace reactor are arranged axially or in the annular gaps of concentric cylindrical grids.

Advantageously, the reaction gas mixture will be subjected to intermediate heating in the tray reactor on its way from one catalyst bed to the next catalyst bed, for example by passing it over heat exchanger ribs heated by hot gases or by passing it through pipes heated by hot combustion gases.

When the tray reactor is otherwise operated adiabatically, it is sufficient for the desired isobutane conversions (≦30 mol %), in particular when the catalysts described in DE-A 19 937 107, in particular those of the exemplary embodiments, are used, to pass the reaction gas mixture into the dehydrogenation reactor preheated to a temperature of from 450 to 550° C. and to maintain it within this temperature range inside the tray reactor. In other words, the entire isobutane dehydrogenation can thus be realized at very low temperatures, which is particularly advantageous for the onstream time of the fixed catalyst beds.

It is even more beneficial to carry out the above-described intermediate heating in a direct way. To this end, a limited amount of molecular oxygen or a gas containing it is added to the reaction gas mixture either before it flows through the first catalyst bed and/or between the subsequent catalyst beds. Depending on the dehydrogenation catalyst used, a limited combustion of the hydrocarbons contained in the reaction gas mixture, any coke or coke-like compounds already deposited on the catalyst surface and/or hydrogen formed in the course of the isobutane dehydrogenation and/or added to the reaction mixture is thus effected (it may also be advantageous from an application point of view to add catalyst beds in the tray reactor which are charged with catalyst which specifically (selectively) catalyzes the combustion of hydrogen (and/or of hydrocarbon) (examples of useful catalysts include those of the documents U.S. Pat. Nos. 4,788,371, 4,886,928, 5,430,209, 55,530,171, 5,527, 979 and 5,563,314); for example, such catalyst beds could be accommodated in the tray reactor in alternation to the beds containing the dehydrogenation catalyst). The heat of reaction released thus allows virtually isothermal operation of the heterogeneously catalyzed isobutane dehydrogenation in a quasi-autothermal manner. As the selected residence time of the reaction gas in the catalyst bed is increased, isobutane dehydrogenation is thus possible at decreasing and substantially constant temperature which allows particularly long onstream times.

In general, oxygen feeding as described above should be carried out in such a manner that the oxygen content of the reaction gas mixture, based on the amount of isobutane and isobutene contained therein, is from 0.5 to 10% by volume. Useful oxygen sources include both pure molecular oxygen and oxygen diluted with inert gas, for example CO, $CO_2$, $N_2$ or noble gases, but in particular also air. The resulting combustion gases generally have an additional dilution effect and thus support the heterogeneously catalyzed isobutane dehydrogenation. The dehydrogenation temperature in the tray reactor in the process according to the invention is generally from 400 to 800° C., and the pressure is generally from 0.2 to 10 bar, preferably from 0.5 to 4 bar and more preferably from 1 to 2 bar. The gas hourly space velocity is generally from 500 to 2000 $h^{-1}$, and in high-load operation even up to 16 000 $h^{-1}$, regularly from 4000 to 16 000 $h^{-1}$.

The isothermicity of the heterogeneously catalyzed isobutane dehydrogenation can be further improved by incorporating closed internals (for example tubular) which have been evacuated before filling in the spaces between the catalyst beds in the tray reactor. It will be appreciated that such internals may also be placed in each catalyst bed. These internals contain suitable solids or liquids which evaporate or melt above a certain temperature, thereby consuming heat, and, when the temperature falls below this value, condense again and thereby release heat.

Another possible method of heating the reaction gas mixture to the required temperature in reaction zone A of the process according to the invention consists in combusting a portion of the isobutane and/or $H_2$ contained therein using molecular oxygen (for example over specific combustion catalysts, for example by simply passing them over and/or through) and to effect the heating to the desired reaction temperature by means of the heat of combustion released in this manner. The resulting combustion products such as $CO_2$, $H_2O$ and also any $N_2$ accompanying the molecular oxygen required for the combustion advantageously take on the role of inert diluent gases.

It will be appreciated that reaction zone A according to the invention can also be realized in a jet pump circulation reactor as described by DE-A 10 211 275. Quite generally, all dehydrogenation variants described in DE-A 10 211 275 are usable in reaction zone A according to the invention.

It is essential to the invention that the isobutane used in reaction zone A is not pure isobutane. Rather, the isobutane used may comprise up to 50% by volume of other gases, for example, ethane, methane, ethylene, n-butanes, n-butenes, propyne, acetylene, propane, propene, $H_2S$, $SO_2$, pentanes, etc. Advantageously, the crude isobutane to be used comprises at least 60% by volume, advantageously at least 70% by volume, preferably at least 80% by volume, more preferably at least 90% by volume and most preferably at least 95% by volume, of isobutane. In particular, a mixture of isobutane, isobutene and cycle gas arising from removals from the product gas mixture A may also be used for the reaction zone A according to the invention.

The product gas mixture A leaving reaction zone A in the process according to the invention comprises at least the components isobutane and isobutene, and also generally molecular hydrogen. Furthermore, it will generally also comprise gases from the group consisting of $N_2$, $H_2O$, methane, ethane, ethylene, propane, propene, CO and $CO_2$ and also possibly $O_2$.

The mixture will generally be at a pressure of from 0.3 to 10 bar and frequently a temperature of from 450 to 500° C.

Quite generally, reactors having passivated interior walls are used for reaction zone A according to the invention. The passivation may be effected, for example, by applying sintered aluminum oxide to the interior wall before dehydrogenation or by using a silicon-containing steel as the reactor material which forms a passivating $SiO_2$ layer on the surface under the reaction conditions. However, passivation may also be achieved in situ by adding small quantities of passivating auxiliaries (for example sulfides) to the reaction zone A charging gas mixture.

The removal of components other than isobutane and isobutene from the product gas mixture A which is essential according to the invention may be carried out in different ways. For instance, separating processes may be applied in succession, each of which is able to remove only individual components.

For example, the hydrogen may be removed by passing the product gas mixture A, optionally after it has been cooled in an indirect heat exchanger (advantageously, the heat removed is used to heat one of the feed gases required for the process according to the invention), over a membrane, generally configured as a tube, which is only permeable toward molecular hydrogen. The molecular hydrogen individually removed in this manner may, if required, be at least partially added to reactor zone A or utilized in another way. In the simplest case, it may be combusted in fuel cells.

Steam contained in the reaction gas mixture A may be individually removed simply in a condensation stage and, if required, recycled at least partially into the reaction zone A.

Removal of hydrogen and steam is possible, for example, by converting hydrogen contained in the reaction gas mixture to steam by selective heterogeneously catalyzed combustion using oxygen over suitable catalysts and then removing it by condensation. When any oxygen in the reaction gas mixture A is used for the abovementioned selective combustion, molecular oxygen contained in the product gas mixture A may be removed at the same time in the abovementioned manner. The disclosure content of U.S. Pat. Nos. 4,788,371, 4,886,928, 5,430,209, 5,530,171, 55,279,979 and 5,563,314 relates to catalysts suitable for such a selective combustion.

In a corresponding manner, CO contained in the reaction gas mixture A can be selectively combusted to $CO_2$ using suitable catalysts and, together with $CO_2$ already contained in the reaction gas mixture A, be removed by scrubbing with a basic liquid. Examples of such basic liquids include aqueous alkali metal hydroxide solutions, aqueous ammonia solutions and organic amines. Nitrogen remaining in the mixture with isobutane and isobutene may, if required, be removed from them by condensation of the hydrocarbons.

A simple method of removing substantially all components of the product gas mixture A other than isobutane and isobutene consists in contacting (for example by simply passing through) the preferably cooled (preferably to temperatures of from 10 to 70° C.) product gas mixture A, for example at a pressure of from 0.1 to 50 bar and a temperature of from 0 to 100° C., with a (preferably high-boiling) organic solvent (preferably hydrophobic) which preferentially absorbs isobutane and isobutene. Subsequent desorption, for example by heating, depressurization-evaporation (flashing) and/or distillation (rectification) or stripping using a gas which is inert in relation to reaction zone B (for example nitrogen and/or steam) and/or molecular oxygen or mixtures of inert gases and molecular oxygen (for example air) recovers the isobutane and isobutene in the mixture which are used to charge reaction zone B.

When the stripping gas used is air or an oxygen-nitrogen mixture where the oxygen content is above 10% by volume it may be sensible to add a gas before or during the stripping process which reduces the explosion range. Particularly suitable gases for this purpose have a heat capacity of $\geq 29$ J/mol·K (based on 25° C. and 1 atm). For example, isobutane may be used as such a gas.

The absorption offgas containing the molecular hydrogen can, for example, again be subjected to membrane separation and then, if required, the hydrogen removed can be used in reaction zone A. The residual gas remaining after the hydrogen removal may, if required, be used as a diluent gas in reaction zones A, B and/or C. The boiling point of the organic absorbent should preferably be $\geq 100°$ C., more preferably $\geq 180°$ C. The absorption may be carried out using columns or else in rotary absorbers. Operation may be effected in cocurrent or countercurrent. Examples of useful absorption columns include tray columns (having bubble cap, centrifugal or sieve trays), columns having structured packings (for example sheet metal packings having a specific surface area of from 100 to 500 $m^2/m^3$, for example Mellapak® 250 Y) and randomly packed columns (for example packed with Raschig shaped bodies). It will be appreciated that trickle and spray towers, graphite block absorbers, surface absorbers such as thick film and thin film absorbers and also rotary columns, plate scrubbers, cross-spray scrubbers and rotary scrubbers may also be considered.

It is advantageous according to the invention when the organic absorbent to be used on the one hand fulfills the boiling point recommendation already given but on the other hand at the same time does not have too high a molecular weight. Advantageously, the molecular weight of the absorbent is $\leq 300$ g/mol.

Examples of absorbents suitable according to the invention include relatively nonpolar organic solvents which preferably contain no polar groups having any external effect. Examples thereof include aliphatic (for example $C_8$- to $C_{18}$-alkenes) or aromatic hydrocarbons, for example middle oil fractions from paraffin distillation, or ethers having bulky groups on the oxygen atom, or mixtures thereof, to which a polar solvent, for example the 1,2-dimethyl phthalates disclosed in DE-A 4 308 087, may be added. Further suitable absorbents include esters of benzoic acid and phthalic acid with straight-chain alkanols containing from 1 to 8 carbon atoms such as n-butyl benzoate, methyl benzoate, ethyl benzoate, dimethyl phthalate and diethyl phthalate, and also heat carrier oils such as diphenyl or diphenyl ether and mixtures of diphenyl and diphenyl ether or chlorine derivatives thereof and triarylalkenes, for example 4-methyl-4'-benzyldiphenylmethane and its isomers 2-methyl-2'-benzyldiphenylmethane, 2-methyl-4'-benzyldiphenylmethane and 4-methyl-2'-benzyldiphenylmethane and mixtures of such isomers. A useful absorbent is a solvent mixture of diphenyl and diphenyl ether, preferably in the azeotropic composition, in particular of about 25% by weight of diphenyl (biphenyl) and about 75% of diphenyl ether, for example the commercially obtainable Diphyl. Frequently, this solvent mixture comprises a solvent such as dimethyl phthalate in an amount of from 0.1 to 25% by weight, based on the entire solvent mixture. Other possible absorbents include octanes, nonanes, decanes, undecanes, dodecanes, tridecanes, tetradecanes, pentadecanes, hexadecanes, heptadecanes and octadecanes.

The paraffin oils having from 8 to 10 carbon atoms described in DE-A 3 313 573 are likewise suitable. Examples of suitable trade products include the products sold by Haltermann including the Halpasols®i, for example Halpasol 250/340 i and Halpasol 250/275 i, and also printing ink distillates under the names PKWF and Printosol.

In order to minimize absorbent losses in removing the isobutene from the absorbate, both the gas phase resulting from the stripping and also a rising gas phase in the distillation or rectification may be scrubbed in countercurrent using water. The scrubbing water used may be steam after its condensation which was contained in the offgas or absorption. Otherwise, the absorptive removal can be carried out as described in WO-0196271 using the example of propane/propene.

An alternative possibility for removing the components other than isobutane and isobutene from product gas mixture A is offered by fractional distillation (rectification). Advantageously, a fractional pressure distillation is carried out at low temperatures. The pressure to be applied may be, for example, from 10 to 100 bar. Useful rectification columns include randomly packed columns, tray columns or columns with structured packing. Useful tray columns include those having dual-flow trays, bubble cap trays or valve trays. Two rectification columns, for example, may be attached in series in a simple manner. In the first column, the components having higher boiling points than isobutane and isobutene are removed as the bottom product. In the second column, isobutane and isobutene may be removed overhead from lower-boiling components.

After the removal required according to the invention of at least 80 mol % of the components other than isobutane and isobutene contained in the product gas mixture A, the resulting product gas mixture A' may be used to charge reaction zone B. If required, the product gas mixture A' may be brought to the reaction temperature required in reaction zone A' by indirect heat exchange.

The methacrolein-containing product gas mixture B formed in reaction zone B is then used without preceding removal of components contained therein to charge a reaction zone C.

The basis for the configuration of the second part of the process according to the invention in two spatially successive reaction zones B and C is the fact that the heterogeneously catalyzed gas phase partial oxidation of isobutene with molecular oxygen to methacrylic acid proceeds in two successive steps along the reaction coordinate, of which the first leads to methacrolein and the second from methacrolein to methacrylic acid.

In each of the two reaction zones B and C, the oxidic catalyst to be used may be optimized in the same manner as the reaction conditions. For instance, for the first oxidation zone, the reaction zone B (isobutene→methacrolein), preference is generally given to a catalyst based on multimetal oxides comprising the element combination Mo—Bi—Fe, while for the second oxidation zone, the reaction zone C (methacrolein→methacrylic acid), preference is normally given to catalysts based on multimetal oxides based on the element combination Mo—P (in particular the heteropolyacids).

Examples of multimetal oxide catalysts suitable for reaction zone B are disclosed by U.S. Pat. Nos. 4,954,650, 5,166,119, DE-A 10 121 592 (multimetal oxide compositions of the formulae I, II and III in the same DE-A), DE-A 10 046 957 (multimetal oxide compositions of the formulae I and II in the same DE-A), DE-A 10 101 695 (multimetal oxide compositions of the formulae I, II and III in the same DE-A), DE-A 10 063 162 (multimetal oxide compositions of the formula I in the same DE-A), DE-A 10 059 713 (multimetal oxide compositions of the formula I in the same DE-A) and DE-A 10 049 873 (multimetal oxide compositions of the formula I in the same DE-A).

A variety of multimetal oxide compositions suitable as catalysts for the reaction zone B can be subsumed by the general formula I $$Mo_{12}Bi_aFe_bX^1_cX^2_dX^3_eX^4_fO_n \quad (I)$$

where the variables are defined as follows:
$X^1$=nickel and/or cobalt,
$X^2$=alkali metal, thallium and/or an alkaline earth metal,
$X^3$=zinc, phosphorus, arsenic, boron, antimony, tin, cerium, lead and/or tungsten,
$X^4$=silicon, aluminum, titanium and/or zirkonium,
a=from 0.5 to 5,
b=from 0.01 to 5, preferably from 2 to 4,
c=from 0 to 10, preferably from 3 to 10,
d=from 0 to 2, preferably from 0.02 to 2,
e=from 0 to 8, preferably from 0 to 5,
f=from 0 to 10 and
n=a number which is determined by the valency and frequency of the elements other than oxygen in I.

The compositions are obtainable in a manner known per se (cf., for example, DE-A 10 121 592) and are customarily used as such shaped into spheres, rings, cylinders or else in the form of coated catalysts, i.e. preshaped inert support particles coated with the active composition.

Examples of suitable unsupported catalyst geometries include solid cylinders and hollow cylinders having an external diameter and a length of from 2 to 10 mm. In the case of the hollow cylinders, a wall thickness of from 1 to 3 mm is advantageous. It will be appreciated that the unsupported catalyst may also have spherical geometry and the sphere diameter may be from 2 to 10 mm. Useful coated catalyst geometries are likewise disclosed by DE-A 10 121 592.

According to the invention, further multimetal oxide compositions useful as catalysts for reaction zone B are compositions of the general formula II $$[Y^1_{a'}Y^2_{b'}O_{x'}]_p[Y^3_{c'}Y^4_{d'}Y^5_{e'}Y^6_{f'}Y^7_{g'}Y^2_{h'}O_{y'}]_q \quad (II)$$

where the variables are defined as follows:
$Y^1$=only bismuth or bismuth and at least one of the elements tellurium, antimony, tin and copper,
$Y^2$=molybdenum and/or tungsten,
$Y^3$=an alkali metal, thallium and/or samarium,
$Y^4$=an alkaline earth metal, nickel, cobalt, copper, manganese, zinc, tin, cadmium and/or mercury,
$Y^5$=iron or iron and at least one of the elemenents chromium, cerium and vanadium,
$Y^6$=phosphorus, arsenic, boron and/or antimony,
$Y^7$=a rare earth metal, titanium, zirconium, niobium, tantalum, rhenium, ruthenium, rhodium, silver, gold, aluminum, gallium, indium, silicon, germanium, lead, thorium and/or uranium,
a'=from 0.01 to 8,
b'=from 0.1 to 30,
c'=from 0 to 4,
d'=from 0 to 20,
e'=from 0 to 20,
f'=from 0 to 6,
g'=from 0 to 15,
h'=from 8 to 16,
x',y'=numbers which are determined by the valency and frequency of elements other than oxygen in II and
p,q=numbers whose ratio p/q is from 0.1 to 10.

In favorable cases, the multimetal oxide compositions II comprise three-dimensional regions which are delimited from their local environment owing to their different composition from their local environment and of the chemical composition $Y^1_{a'}Y^2_{b'}O_{x'}$ and whose maximum diameter (longest line connecting two points on the surface (boundary layer) of the region and passing through the main focus of the region) is from 1 nm to 100 μm, frequently from 10 nm to 500 nm or from 1 μm to 50 or 25 mm.

With regard to the shaping, the remarks made on multimetal oxide compositions I catalysts apply to multimetal oxide compositions II catalyts.

The preparation of multimetal oxide compositions II catalysts is described, for example, by EP-A 575897, DE-A 19855913, DE-A 10 046 957 and DE-A 10 121 592.

Reaction zone B is most easily realized by a tube bundle reactor whose catalyst tubes are charged with catalyst. The configuration may be entirely similar to the teaching of EP-A 911313, EP-A 979813, EP-A 990636 and DE-A 2830765 for the partial oxidation of propylene to acrolein. Otherwise, reaction zone B may be configured as taught in U.S. Pat. Nos. 4,954,650 and 5,166,119.

The reaction temperature is generally from 250 to 450° C. The reaction pressure is advantageously from 0.5 to 5, frequently from 1 to 3, bar. The gas hourly space velocity (1 at STP/l·h) on the oxidation catalysts is frequently from 1500 to 2500 h$^{-1}$ or 4000 h$^{-1}$.

In principle, reaction zone B may also be configured as described for similar reactions, for example, in DE-A 19837517, DE-A 19910506, DE-A 19910508 and also DE-A 19837519.

Customarily, the external heating, if appropriate in multizone reactor systems, is adjusted in a manner known per se to the specific reaction gas mixture composition and also catalyst charge.

The molecular oxygen required in the reaction zone B necessary for the invention is normally added in advance in its entirety to the charging gas mixture of reaction zone B.

Normally, a molar isobutene:molecular oxygen ratio in the charging gas for reaction zone B of from 1:1 to 3, frequently from 1:1.5 to 2.5, is set.

An excess (based on the stoichiometry of the gas phase partial oxidation) of molecular oxygen generally has an advantageous effect on the kinetics of the gas phase oxidation in reaction zone B. In contrast to the conditions in the reaction zone A to be applied according to the invention, the thermodynamic ratios in reaction zone B are substantially not influenced by the molar reactant ratio, since the heterogeneously catalyzed gas phase partial oxidation of isobutene to methacrolein is under kinetic control.

In principle, it is therefore also possible, for example, to initially charge the isobutene into reaction zone B in a molar excess relative to the molecular oxygen. In this case, the excess isobutene actually assumes the role of a diluent gas.

A useful source for the molecular oxygen required overall in reaction zone B which is normally admixed with product gas mixture A' before it is used to charge reaction zone B is in particular oxygen diluted with molecular nitrogen. Advantageously, air will be used as the oxygen source at least to cover part of the need for molecular oxygen, since the nitrogen also to be used in reaction zone B may be introduced into the reaction system in this manner in a very simple way.

However, a portion of the molecular oxygen required overall in reaction zone B may also already be contained in the product gas mixture A' introduced into reaction zone B. However, preference is given to no more oxygen being contained therein. Further useful oxygen sources usable in the reaction zone include molecular oxygen diluted with inert gases such as $CO_2$, CO, noble gases, $N_2$ and/or saturated hydrocarbons. An example of such an oxygen source is a cycle gas diverted from the process according to the invention and recycled into reaction zone B.

In the process according to the invention, the source for molecular oxygen in the downstream reaction zone B, apart from any molecular oxygen already contained in the product gas mixture A', is advantageously at least partially and preferably exclusively air.

The metering of cold air at room temperature into the hot product gas mixture A' in the process according to the invention may, if required, be used to cool the product gas mixture A' on its way into reaction zone B.

The product gas mixture B leaving reaction zone B to be used according to the invention is generally substantially composed of the target product methacrolein or a mixture thereof with methacrylic acid, unconverted molecular oxygen, isobutane, unconverted isobutene (the molar conversion of isobutene in the reaction zone B according to the invention is preferably ≧96 or ≧97 mol %, more preferably ≧98 mol % and most preferably ≧99 mol %), molecular nitrogen (optionally molecular hydrogen), steam formed as a by-product and/or used as a diluent gas, carbon oxides as a by-product and/or used as a diluent gas, and also small amounts of other lower aldehydes, hydrocarbons and other inert diluent gases. However, the isobutyraldehyde and isobutyric acid contents are minimized in accordance with the invention. It is essential to the invention that the molar conversion of isobutene in the reaction zone B is ≧95 mol %.

Advantageous catalysts for reaction zone C are disclosed, for example, by DE-A 4405060, U.S. Pat. Nos. 5,166,119, 5,153,162, 4,954,650, 4,558,028 and DE-A 19 815 279. These patents also teach the use of such catalysts. As well as molybdenum and phosphorus, they customarily comprise metallic and transition metallic elements, in particular copper, vanadium, arsenic, antimony, cesium and also potassium (cf. DE-A 4329907, DE-A 2610249, JP-A 7/185354).

DE-A 19 922 113 suggests multimetal oxide compositions of the general formula III $$[A]_p[B]_q \qquad (III)$$

where the variables are defined as follows:
A: $MO_{12}X_a^1X_b^2X_c^3X_d^4X_e^5O_x$
B: $Mo_fX_g^6X_h^7O_y$
$x^1$=H, of which up to 97 mol % may be replaced by ammonium, K, Rb and/or Cs,
$X^2$=V, Nb, Ta, W and/or Re,
$X^3$=B, Si, P, Ge, As and/or Sb,
$X^4$=Cr, Mn, Fe, Co, Ni, Cu, Zn, Mg, Ca, Sr and/or Ba,
$X^5$=S,
$X^6$=Cu, Fe, Co, Ni, Zn, Cd, Mn, Mg, Ca, Sr and/or Ba,
$X^7$=Nb, Ta and/or Sb,
a=from 1 to 3,
b=from 0.1 to 2,
c=from 0 to 5,
d=from 0 to 1,
e=from 0 to 1,
f=from 0 to 2,
g=from 0.5 to 1.5,
h=from 2 to 4,
x,y=numbers which are determined by the valency and frequency of the elements other than oxygen in (I),
p=1 and q=0 or
p, q are integers other than zero whose ratio p/q is from 160:1 to 1:1 and the standard deviation of the stoichiometric coefficients a of the $X^1$ variables of individual crystallites within the component A of the multimetal oxide composition is less than 0.40, preferably less than 0.20, in particular less than 0.11.

The compositions preferably comprise the fraction $[A]_p$ in the form of three-dimensional regions A of chemical composition A which are delimited from their local environment owing to their different chemical composition and the fraction $[B]_q$ in the form of three-dimensional regions B of chemical composition B which are delimited from their local environment owing to their different chemical composition from their local environment, and the regions A and B are distributed relative to each other as in a finely divided mixture of A and B.

DE-A 4405060 recommends similar multimetal oxide compositions for a reaction zone C. Like the multimetal oxide catalysts for reaction zone B, the multimetal oxide catalysts for reaction zone C are customarily used as such shaped into spheres, rings or cylinders or else in the form of coated catalysts, i.e. preformed inert support particles coated with the active composition.

Examples of suitable unsupported catalyst geometries include solid cylinders and hollow cylinders having an external diameter and a length of from 2 to 10 mm. In the case of the hollow cylinders, a wall thickness of from 1 to 3 mm is advantageous. It will be appreciated that the unsupported catalyst may also have spherical geometry and the sphere diameter may be from 2 to 10 mm. Examples of useful coated catalyst geometries are those disclosed by DE-A 10 121 592.

The simplest way of realizing reaction zone C, as in the case of reaction zone B, is a tube bundle reactor, and so all remarks made in relation to the tube bundle reactor of reaction zone B are also similarly valid for a tube bundle reactor of reaction zone C.

With regard to the flow of reaction gas and heating medium (for example salt bath), the tube bundle reactors recommended for both reaction zone B and reaction zone C may be operated either in cocurrent or else in countercurrent. It will be appreciated that crosscurrent flows may also be superimposed. A meandering flow of the temperature medium around the catalyst tubes is particularly advantageous and, viewed over the reactor, may again be in cocurrent or in countercurrent to the reaction gas mixture.

A particularly simple way of realizing the reaction zones B and C is accordingly a tube bundle reactor within which the catalyst charge changes correspondingly along the individual catalyst tubes. The charge of the catalyst tubes with catalyst may optionally be interrupted by an inert bed (EP-A 911313, EP-A 979813, EP-A 990636 and DE-A 2830765 teach such a procedure in an equivalent manner using the example of partial oxidation of propylene to acrylic acid). In the case of this way of realization, the molecular oxygen required in reaction zone C already has to be contained in the charging gas mixture for reaction zone B.

However, preference is given to realizing the two reaction zones B and C in the form of two tube bundle systems connected in series. These may optionally be in one reactor and one tube bundle may be connected to the other tube bundle by a bed (advantageously accessible on foot) of inert material which is not accommodated in the catalyst tubes. While the catalyst tubes are generally purged through by a heat carrier, this does not reach an inert bed installed as described above. However, the two catalyst tube bundles will advantageously be accommodated in spatially separated reactors. There may be an intermediate cooler between the two tube bundle reactors in order to reduce any continued methacrolein combustion in the product gas mixture which leaves reaction zone B. Instead of tube bundle reactors, plate heat exchanger reactors having salt and/or evaporative cooling, as described, for example, by DE-A 19929487 and DE-A 19952964, may also be used.

The reaction temperature in reaction zone C is generally from 230 to 350° C., frequently from 250 to 320° C. The reaction pressure in reaction zone C is advantageously from 0.5 to 5, frequently from 1 to 3 or 2, bar. The gas hourly space velocity (1 at STP/l·h) on the oxidation catalysts of reaction C of charging gas mixture is frequently from 1000 to 2500 h$^{-1}$ or to 4000 h$^{-1}$.

As already mentioned, the molecular oxygen required overall as an oxidizing agent in reaction zone C may already be added in advance to the charging gas mixture of reaction zone B in its entirety. However, it will be appreciated that supplementation with oxygen may also be effected after reaction zone B. The latter possibility is used in particular when the two reaction zones B and C are realized in the form of two tube bundle systems in series.

Since the molecular oxygen used in reaction zone B is also a component of the charging gas mixture of reaction zone C, such oxygen supplementation may be carried out by means of pure molecular oxygen. A further oxygen source usable for such supplementation purposes is molecular oxygen diluted with inert gases such as $CO_2$, CO, noble gases, $N_2$ and/or saturated hydrocarbons. An example of such an oxygen source may be a cycle gas diverted from the process according to the invention and recycled into reaction zone C. According to the invention, preference is given to using air for such oxygen supplementation.

Even in reaction zone C, an excess (based on the reaction stoichiometry) of molecular oxygen generally has an advantageous effect on the kinetics of the gas phase oxidation. Preference is given to setting a molar methacrolein:molecular oxygen ratio in reaction zone C of from 1:1 to 3, frequently from 1:1.5 to 2.5.

Frequently, the process according to the invention is carried out in such a manner that at least 50 mol %, preferably at least 60 mol %, of the total amount of molecular oxygen in the product gas mixture C which has been introduced in the various reaction zones has been converted.

Frequently, the process according to the invention in reaction zone C will be performed at a molar methacrolein:molecular oxygen:steam:isobutane:molecular nitrogen:other diluent gas ratio of 2–5:5–15:0–20:5–25:20–80:0–6.

However, reaction zones B and C may in principle also be formally combined into a single reaction zone. In this case, the two reaction steps (isobutene→methacrolein; methacrolein→methacrylic acid) are effected in an oxidation reactor which is charged with a catalyst which is able to catalyze the reaction of both successive reaction steps.

The metering of cold (at ambient temperature) air into the hot product gas mixture B in the process according to the invention may also be used as a direct way of cooling the product gas mixture B before it is used to charge reaction zone C.

The product gas mixture C leaving reaction zone C is generally composed substantially of methacrylic acid, methacrolein, unconverted molecular oxygen, isobutane, molecular nitrogen, steam formed as a by-product and/or used as a diluent gas, (optionally molecular hydrogen), carbon oxides formed as a by-product and/or used as a diluent gas, and also small quantities of other lower aldehydes, hydrocarbons and other inert diluent gases. Its isobutyraldehyde and isobutyric acid contents are minimized in accordance with the invention.

The methacrylic acid may be removed from the product gas mixture C in a manner known per se.

For example, product gas mixture C (which may have an exit temperature of, for example, 220° C.) may first be cooled by direct contact with a 10% by weight aqueous solution of methacrylic acid which may be polymerizationinhibited, for example, by the addition of small amounts of hydroquinone monomethyl ether (MEHQ) and have a temperature of 80° C. To this end, the aqueous methacrylic acid solution is sprayed into the product gas mixture C in an apparatus substantially free of internals and passed in cocurrent with it. Mist which forms may be separated from the gas phase in two Venturi precipitators. Afterwards, the cooled product gas mixture is then passed into the bottom of an absorption column, for example a randomly packed column. At the top of the column, water which contains the polymerization inhibitors dissolved is added as the absorbing liquid in countercurrent to the rising gas. The top temperature may be, for example, 63° C. and the bottom temperature, for example, 70° C.

Together with medium- and high-boiling by-products such as acetic, propionic, acrylic, maleic, fumaric, citraconic and formic acid and also formaldehyde and any isobutyraldehyde and isobutyric acid formed, the methacrylic acid is removed in the absorber from the gas phase into the aqueous phase.

The methacrylic acid can be removed extractively from the from 10 to 20% by weight aqueous methacrylic acid solution withdrawn from the bottom of the absorber using suitable extractants, for example ethylhexanoic acid, and subsequently isolated rectificatively.

The residual gas leaving the absorber at the top generally comprises isobutane, isobutene, methacrolein, $O_2$, (possibly $H_2$), $N_2$, CO, $CO_2$, $H_2O$, noble gases and also other lower aldehydes and hydrocarbons.

The methacrolein can be removed therefrom by means of subsequent scrubbing with water and freed again from the scrubbing water by stripping using air and recycled with the air into reaction zone C.

According to the invention, the residual gas remaining after the methacrylic acid removal which normally comprises unconverted isobutane and isobutene will preferably be recycled as such into the reaction zone A. However, it is also possible in the process according to the invention to first substantially remove the isobutane and isobutene generally contained in the residual gas remaining after the methacrylic acid removal from other gases such as $O_2$ (possibly $H_2$), $N_2$, CO, $CO_2$, noble gases, etc. contained therein by absorption with subsequent desorption and/or stripping and also absorbent reuse in a high-boiling hydrophobic organic solvent and then to recycle them into reaction zone A. If required, the remaining other gases from the mixture may be recycled as diluent gas into reaction zones B and/or C. However, they may also be discharged, for example incinerated.

In general, solvents useful as absorbents for the abovementioned purpose include relatively nonpolar organic solvents, for example aliphatic hydrocarbons, which preferably have no external polar groups, and also aromatic hydrocarbons. In general, it is desirable that the absorbents have a very high boiling point and at the same time very high solubility for isobutane and/or isobutene and very low solubility for the other residual gas components.

Examples of useful absorbents include aliphatic hydrocarbons, for example $C_8$–$C_{20}$-alkanes or -alkenes, or aromatic hydrocarbons, for example middle oil fractions from paraffin distillation, or ethers having bulky groups on the oxygen atom, or mixtures thereof, to which a polar solvent, for example the 1,2-dimethyl phthalate disclosed in DE-A 4308087. Further suitable absorbents include esters of benzoic acid and phthalic acid with straight-chain alkanols containing from 1 to 8 carbon atoms such as n-butyl benzoate, methyl benzoate, ethyl benzoate, dimethyl phthalate and diethyl phthalate, and also heat carrier oils such as diphenyl or diphenyl ether and mixtures of diphenyl and diphenyl ether or chlorine derivatives thereof and triarylalkenes, for example 4-methyl-4'-benzyldiphenylmethane and its isomers 2-methyl-2'-benzyldiphenylmethane, 2-methyl-4'-benzyldiphenylmethane and 4-methyl-2'-benzyldiphenylmethane and mixtures of such isomers. A useful absorbent is also a solvent mixture of diphenyl and diphenyl ether, preferably in the azeotropic composition, in particular of about 25% by weight of diphenyl (biphenyl) and about 75% by weight of diphenyl ether, for example the commercially obtainable Diphyl. Frequently, this solvent mixture comprises a solvent such as dimethyl phthalate in an amount of from 0.1 to 25% by weight, based on the entire solvent mixture. Particularly useful absorbents also include octanes, nonanes, decanes, undecanes, dodecanes, tridecanes, tetradecanes, pentadecanes, hexadecanes, heptadecanes and octadecanes, and tetradecanes in particular have proven particularly useful. It is advantageous when the absorbent used on the one hand attains the abovementioned boiling point and on the other hand at the same time does not have too high a molecular weight. Advantageously, the molecular weight of the absorbent is $\leq 300$ g/mol. The paraffin oils having from 8 to 10 carbon atoms described in DE-A 3313573 are likewise suitable. Examples of useful trade products include the products sold by Haltermann including Halpasols®i, for example Halpasol 250/340i and Halpasol 250/275i, and also printing ink distillates sold as PKWF and Printosol.

The performance of the absorption is subject to no particular restrictions. All processes and conditions familiar to those skilled in the art may be used. Preference is given to contacting the gas mixture with the absorbent at a pressure of from 1 to 50 bar, preferably from 2 to 20 bar, more preferably from 5 to 10 bar, and a temperature of from 0 to 100° C., in particular from 30 to 50° C. The absorption may be carried out in absorption columns, for example tray columns having bubble cap and/or sieve trays, columns having structured packings or randomly packed columns, in trickle and spray towers, graphite block absorbers, surface absorbers such as thick film and thin film absorbers and also plate scrubbers, cross-spray scrubbers and rotary scrubbers. It may also be advantageous to carry out the absorption in a bubble column with or without internals.

The isobutane and/or isobutene may be removed from the absorbate by stripping, depressurization-evaporation (flashing) and/or distillation (rectification).

Gases suitable for stripping are in particular those which may be recycled into reaction zone A together with the isobutane and isobutene.

Such gases include nitrogen, air, oxygen, oxygen/nitrogen mixtures, isobutane and steam. When air or oxygen/nitrogen mixtures are used where the oxygen content is above 10% by volume, it may be sensible to add a gas which reduces the explosion range before or during the stripping process. Particularly suitable gases for this purpose have a heat capacity of $\geq 29$ J/mol-K (based on 25° C. and 1 atm). For example, isobutane may also be used as such a gas.

The isobutane and/or isobutene may also be removed from the absorbate by a distillation. In order to minimize absorbent losses, both the gas phase resulting from the stripping and a rising gas phase resulting from distillation may be scrubbed in countercurrent using water. The scrubbing water used may be condensed steam contained in the residual gas.

Otherwise, the procedure may be as described in WO-0196271 using the example of propane/propene.

Further possible methods of removing isobutane and/or isobutene from the residual gas are adsorption, rectification and partial condensation. Preference is given to carrying out a fractional pressure distillation at low temperatures. The pressure to be applied may be, for example, from 10 to 100 bar. Useful rectification columns include randomly packed columns, tray columns or columns having structured packing. Useful tray columns include those having dual-flow trays, bubble cap trays or valve trays. The reflux ratio may be, for example, from 1 to 10. Examples of other possible separating methods include pressure extraction, pressure swing adsorption, pressure scrubbing and partial condensation. For the purposes of a fractional distillation, the separating line may, for example, be defined in such a manner that substantially all of those components whose boiling point is lower than the boiling point of isobutene are removed at the top of the rectification column. These components will primarily be the carbon oxides CO and $CO_2$ and also unconverted oxygen and $N_2$. Steam may be recycled together with isobutane and isobutene into reaction zone A.

A more comprehensive description of the above-outlined removal of methacrylic acid and methacrolein from a product gas mixture such as product gas mixture C can be found in EP-B 297445

However, it will be appreciated that the separating processes of U.S. Pat. Nos. 4,925,981 and 4,554,054 may also be used for this purpose.

It is common to all these processes that a residual gas comprising unconverted isobutane and generally isobutene remains after the methacrylic acid removal. According to the invention, preference is given to recycling this, as already mentioned, as such into reaction zone A.

It will be appreciated that the process according to the invention may also be carried out by recycling only a portion of the residual gas unchanged into reaction zone A and removing isobutane and isobutene in the mixture only from the remaining portion and likewise recycling them into reaction zone A.

If the gas containing isobutane and isobutene to be recycled into reaction zone A still contains carbon monoxide, this may be catalytically selectively combusted to $CO_2$ before (or after) entry into reaction zone A. The heat of reaction released may be used to heat to the dehydrogenation temperature.

Catalytic postcombustion of CO contained in the residual gas to $CO_2$ may also be recommendable when removal of the carbon oxides from the residual gas is sought before it is recycled into reaction zone A (or another zone), because $CO_2$ can be comparatively easily removed (for example by scrubbing with a basic liquid).

When dehydrogenation catalysts are used which are sensitive toward oxygen or oxygen-containing compounds, these oxygenates will be removed from the residual gas before recycling of the residual gas into reaction zone A. This is unnecessary for the catalysts particularly recommended for the catalytic dehydrogenation in this document.

It will be appreciated that isobutane and/or isobutene removed or residual gas containing these gases may also be utilized for purposes other than recycling to reaction zone A (for example for preparing isobutanol or for combustion for the purposes of energy generation).

The advantage according to the invention of reduced isobutyraldehyde and isobutyric acid by-production is substantially independent of the multimetal oxide catalysts used in reaction zones B and C. Preference is given to using those multimetal oxide catalysts which are explicitly mentioned in this document. This advantage is also substantially independent of whether the volume-specific catalyst activity in reaction zones B and C is kept constant or increases or decreases along the reaction coordinate.

In general, operation is effected in reaction zone C of the process according to the invention at a molar methacrolein oxygen:steam:inert gas ratio of (2–5):(5–15):(0–20):(5–25):(20–80):(0–6), more preferably of (3–4):(6–10):(10–20):(10–20):(40–70):(0–4). Like reaction zone B, reaction zone C may be realized not only in fixed bed reactors, but also in fluidized bed reactors.

The methacrolein conversion in reaction zone C based on single reactor pass (as always in this document) is customarily from 60 to 90 mol %.

It is quite generally the case that when gases recycled into the reaction zone A comprise $O_2$, this oxygen may be used in the reaction zone to selectively combust combustible substances such as hydrocarbon, coke, CO or preferably $H_2$ in reaction zone A, in order to thus generate the heat of dehydrogenation required in reaction zone A. Advantageously, the methacrolein oxidation will be carried out with an appropriate oxygen excess so that the above-mentioned residual gas recycled into reaction zone A has a sufficient amount of oxygen for this purpose.

Frequently, the process according to the invention will be carried out in such a manner that at least 50 mol %, preferably at least 60 mol %, of the total amount of molecular oxygen introduced into the different reaction zones has been converted in product gas mixture C.

EXAMPLES

1. Preparation of a Dehydrogenation Reactor

A solution of 11.993 g of $SnCl_2.2H_2O$ and 7.886 g of $H_2PtCl_6.6H_2O$ in 600 ml of ethanol are poured over 1000 g of a spalled $ZrO_2.SiO_2$ mixed oxide.

The mixed oxide has a $ZrO_2/SiO_2$ weight ratio of 95:5. The mixed oxide is manufactured by Norton (USA).

The mixed oxide has the following specification:

Type AXZ 311070306, Lot No. 2000160042, sieve fraction from 1.6 to 2 mm, BET surface area: 86 $m^2/g$, pore volume: 0.28 ml/g (mercury porosimetry measurement).

The supernatant ethanol is taken off on a Rotavapor by rotating in a water jet pump vacuum (20 mbar) at a water-bath temperature of 40° C. Drying is then effected at 100° C. for 15 h and then calcining at 560° C. over 3 h, both under stationary air. A solution of 7.71 g of $CsNO_3$, 13.559 g of $KNO_3$ and 98.33 g of $La(NO_3)_3.6H_2O$ in 2500 ml of $H_2O$ is then poured over the dry solids. The supernatant water is taken off on a Rotavapor by rotating in a water jet pump vacuum (20 mbar) at a water temperature of 85° C. Drying is then effected at 100° C. for 15 h and then calcining at 560° C. over 3 h, both under stationary air.

The resulting catalyst precursor has a composition of $Pt_{0.3}Sn_{0.6}Cs_{0.5}K_{0.5}La_{3.0}$ (stoichiometric coefficients represent weight ratios) on $(ZrO_2)_{95}.(SiO_2)_5$ (stoichiometric coefficients represent weight ratios).

20 ml of the catalyst precursor obtained are used to charge a vertical tube reactor (reactor length: 800 mm; wall thickness: 2 mm, internal diameter: 20 mm; reactor material: internally alonized (i.e. aluminum oxide-coated) steel tube; heating: electrical (furnace from HTM Reetz, LOBA 1100-28-650-2) to a longitudinal average length of 650 mm; length of the catalyst bed: 75 mm; position of the catalyst bed: at the longitudinal midpoint of the tubular reactor; filling of the remaining reactor volume above and below with steatite spheres (inert material) of 4–5 mm diameter, supported from below on a catalyst base).

The reaction tube is then charged at an external wall temperature along the heating zone of 500° C. under closed loop control (based on a tube flowed through by an identical inert gas stream) with 9.3 l/h (STP) of hydrogen over 30 min. The hydrogen is then replaced at constant wall temperature firstly by a 23.6 l/h (STP) stream of 80% by volume of nitrogen and 20% by volume of air over 30 min and then by an identical stream of pure air over 30 min. While maintaining the wall temperature, purging is then effected using an identical stream of $N_2$ over 15 min and finally reduction using 9.3 l/h (STP) of hydrogen again over 30 min. The activation of the catalyst precursor is then complete. This results in a dehydrogenation reactor charged with dehydrogenation catalyst A (reaction zone A reactor).

2. Preparation of a Reaction Zone B Reactor a) Preparation of a Starting Composition B1

To prepare the starting catalyst B1, 2000 g of $(NH_4)_6Mo_7O_{24} \cdot 4H_2O$ are dissolved in portions in 5.4 l of water at 60° C. and admixed with stirring with 9.2 g of a 47.5% by weight aqueous KOH solution at 20° C. and then with 387.8 g of a 47.5% by weight aqueous $CsNO_3$ solution at 20° C. while maintaining the temperature at 60° C. (starting solution 1). A starting solution 2 is prepared by stirring 1123.6 g of an aqueous iron nitrate solution (13.8% by weight of Fe) into 2449.5 g of an aqueous cobalt nitrate solution (12.5% by weight of Co) at 60° C. while maintaining the temperature at 60° C.

Within a period of 30 min, the starting solution 2 at 60° C. is stirred into the starting solution 1 at 60° C. 15 min after stirring has ended, 157.0 g of silica sol (density: 1.39 g/ml; pH=8.8; alkali metal content: ≦0.5% by weight, 50.0% by weight of $SiO_2$; manufacturer: Dupont; Ludox®TM) are stirred into the aqueous suspension obtained (at 60° C.). The aqueous mixture is then stirred for a further 15 minutes. The aqueous suspension is then spray-dried (exit temperature: 110° C., spray dryer from Niro DK; model: Niro A/S Atomizer Mobile Minor, centrifugal atomizer from Niro, DK), to obtain a spray powder of particle size from 20 μm to 25 μm having a glow loss (3 h at 600° C. under air) of about 30% by weight. This spray powder forms the starting composition B1.

b) Preparation of a Starting Composition B2

1715.6 g of tungstic acid (72.94% by weight of W) are added in portions to 6344.6 g of an aqueous bismuth natrate solution in nitric acid (free nitric acid: 4% by weight, density: 1.24 mg/l; 11.2% by weight of bismuth) at 20° C. with stirring. This gives an aqueous suspension which is stirred at 20° C. for a further 2 h. This is then dried by spray drying (exit temperature: 110° C., manufacturer: Niro DK; model: Niro A/S Atomizer Mobile Minor, centrifugal atomizer from Niro, DK). In this manner, a spray powder of particle size from 20 μm to 25 μm is obtained which has a glow loss (3 h at 600° C. under air) of about 12% by weight. After addition of 37 g of water, 400 g of this powder are kneaded using a Werner & Pfleiderer LUK 075 kneader (kneader has two sigma blades operating in contrarotation) for 30 min. After the kneading, the kneaded material is roughly divided and dried for 2 h in a drying cabinet (Binder, DE, type: FD 53) at 120° C. The entire amount of the dried material is calcined in a muffle furnace from Nabertherm, capacity about 120 l, at 800° C. over 2 h under an air stream of 1000 l/h (STP). The air stream is at about 20° C. when it is passed into the muffle furnace. Heating to the calcination temperature is effected linearly from 25° C. within 8 h.

The calcined material is then milled to a number average particle size (narrow distribution, longest dimension) of about 5 μm and mixed with 1% by weight (based on the $SiO_2$-free composition) of finely divided $SiO_2$ (bulk density: 150 g/l; number average particle size: 10 μm (longest dimension, narrow distribution); BET surface area: 100 m²/g).

This mixture forms the starting composition B2 c) Catalyst Preparation 1096 g of starting composition B1 and 200 g of starting composition B2 are mixed homogeneously with the addition of (based on the overall composition of B1 and B2 used) 1.5% by weight of finely divided graphite (according to sieve analysis min. 50% by weight <24 μm; 24 μm <max. 10% by weight <48 μm; 5% by weight >48 μm; BET surface area: 10 m²/g) as a tableting aid. This gives a mixture which has the following molar elemental stoichiometry (after calcination):

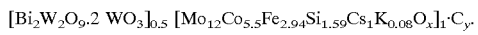

$[Bi_2W_2O_9 \cdot 2\ WO_3]_{0.5}\ [Mo_{12}Co_{5.5}Fe_{2.94}Si_{1.59}Cs_1K_{0.08}O_x]_1 \cdot C_y$.

Circular solid tablets of diameter 16 mm and height 3 mm are pressed from the mixture. The pressing pressure is 9 bar. The tablets are comminuted and sieved through a sieve (0.8 mm mesh size). The material which passes through the sieve, after addition of 2% by weight of graphite (based on the weight of the material which passes through the sieve) is tableted in a tablet pressing machine (Kilian S100, pressing force: 15–20 N) into cylindrical rings of geometry 5 mm (external diameter)×3 mm (height)×2 mm (hole diameter).

150 g of these rings are calcined in a forced-air oven (Nabertherm, about 80 l capacity) as follows:

a) linear heating is effected from room temperature to 180° C. within 2 h and this temperature is maintained for 1 h;
b) linear heating is then effected from 180° C. to 210° C. within 1 h and this temperature is maintained for 1 h;
c) linear heating is then effected from 210° C. to 250° C. within 1 h and this temperature is maintained for 1 h;
d) linear heating is then effected from 250° C. to 450° C. within 1.5 h and this temperature is maintained for 10 h;
e) finally, the oven is left to cool by itself to room temperature (about 25° C.).

During the entire calcination, 150 l/h (STP) of air are passed through the oven.

The end product forms the multimetal oxide catalyst B to be used in reaction zone B.

d) Charging of the Reaction Zone B Reactor

A vertical reactor tube (tube length: 1500 mm; wall thickness: 2.5 mm; internal diameter: 15 mm; reactor material: V2A steel; in a furnace from HTM Reetz at a longitudinal midpoint length of 1300 mm, the remaining tube length at the tube entrance and the remaining tube length at the tube exit are heated with electrical heating bands) is charged with 100 g of catalyst B. The length of the catalyst bed is 650 mm. The position of the catalyst bed in the reaction tube is at the longitudinal midpoint. The remaining reaction tube volume above and below is filled with steatite spheres (inert material; 2–3 mm diameter), and the entire reaction tube charge is supported from below on a catalyst base of 10 cm height.

3. Preparation of a Reaction Zone C Reactor a) Preparation of a Starting Composition C1

4620 g of $(NH_4)_6Mo_7O_{24} \cdot 4H_2O$ and 153.2 g of $NH_4VO_3$ are dissolved at 60° C. with constant stirring in 5 l of water preheated to 60° C. While maintaining the temperature at 60° C., 421.7 g of a 76% by weight aqueous $H_3PO_4$ solution are added dropwise to this solution within 1 min with stirring. First 10.9 g of diammonium sulfate and then 317.8 g of pulverulent $Sb_2O_3$ (senarmontite) are then incorporated. The resulting mixture is then heated to 90° C. within 30 min (mixture 1). In parallel, 424.9 g of $CsNO_3$ are dissolved at 90° C. in 850 ml of water preheated to 90° C. to give a solution 1. While maintaining the temperature at 90° C., 446.5 g of an aqueous copper nitrate solution (15.5% by weight of copper) at 90° C. are added dropwise to mixture 1 within 4 min with continuous stirring. Spray-drying is then effected at an exit temperature of 110° C. (Niro DK, model: Niro A/S Atomizer Mobile Minor, centrifugal atomizer from Niro, DK). A spray powder of particle size from 20 to 30 μm is obtained which forms the starting composition C1 and has the following molar elemental stoichiometry (after calcination):

$$Mo_{12}P_{1.5}V_{0.6}Cs_1Cu_{0.5}Sb_1S_{0.04}O_x.$$

b) Preparation of a Starting Composition C2

880 g of pulverulent $Sb_2O_3$ (senarmontite) having an Sb content of 83% by weight are suspended with stirring in 4 l of water at 20° C. While maintaining the temperature at 20° C., a solution of 670.5 g of $Cu(NO_3)_2 \cdot 2H_2O$ in 4 l of water is stirred into the suspension. This gives an aqueous suspension which is stirred at 80° C. for a further 2 h and is then spray-dried (exit temperature: 110° C., Niro DK, model: Niro A/S Atomizer Mobile Minor, centrifugal atomizer from Niro, DK). The spray powder has a particle size of 20–30 μm. 700 g of the spray powder are thermally treated in a cylindrical rotary furnace (length of the calcination chamber 0.50 m; internal diameter: 12.5 cm) while passing through 200 l/h (STP) of air as follows: within 1 h, linear heating is effected to 150° C. Linear heating is then effected to 200° C. within 4 h. Afterwards, linear heating is effected to 300° C. within 2 h and then to 400° C. within 2 h. Finally, linear heating is effected to 900° C. within 48 h.

After cooling to room temperature, a powder is obtained which has a specific BET surface area of 0.3 m²/g. This powder forms the starting composition C2 and substantially has the diffraction reflections of $CuSb_2O_6$ (comparative spectrum 17-0284 from the JCPDS-ICDD index). The starting composition C2 has the following molar elemental stoichiometry:

$$CuSb_2O_6.$$

c) Catalyst Preparation

The amounts of the starting composition C1 and the starting composition C2 corresponding to the mixing stoichiometry (after calcination) $(Mo_{12}P_{1.5}V_{0.6}Cs_1Cu_{0.5}Sb_1S_{0.04}O_x)_1 \cdot (Cu_1Sb_2O_6)_{0.5}$ are intimately mixed. 2% by weight of finely divided graphite (according to sieve analysis, min. 50% by weight <24 μm; 24 μm <max. 10% by weight <48 μm; 5% by weight >48 μm; BET surface: 10 m²/g) are then admixed into 500 g of the abovementioned mixture as a tableting aid.

A tablet pressing machine (Kilian S 100) is used without the addition of further additives to shape cylindrical rings of geometry 7 mm (external diameter)×7 mm (height)×3 mm (hole diameter) from the mixture.

500 g of the rings are then thermally treated in a forced-air oven (Nabertherm, capacity about 80 l) under a constant air stream (500 l/h (STP)·kg of solid) as follows: heating is effected at 4° C./min from 25° C. to 270° C. while maintaining the intermediate temperatures of 180° C. and 220° C. and the end temperature of 270° C. for 30 minutes each. Finally, the temperature is increased at a rate of 2° C./min to 370° C. and this temperature is maintained over 6 h.

Cooling is then effected to room temperature and the hollow cylinders are processed to spall having a longest dimension of 1.6–3 mm. This spall forms a multimetal catalyst C to be used in reaction zone C.

d) Charging of the Reaction Zone C Reactor

A vertical reactor tube (tube length: 1800 mm; wall thickness: 1 mm; internal diameter: 8 mm; reactor material: V2A steel; in a furnace from HTM Reetz at a longitudinal midpoint length of 1600 mm) is charged with 75 g of the multimetal oxide catalyst C. The length of the catalyst bed is 1000 mm. The position of the catalyst bed in the reaction tube is at the longitudinal midpoint. Above and below, the remaining reaction tube volume is filled with steatite spheres (inert material; diameter: 2–3 mm), and the entire reaction tube charge is supported from below on a catalyst base of height 10 cm. The remaining tube length at the tube entrance and the remaining tube length at the tube exit is heated with electrical heating bands.

4. Performance of the Process According to the Invention

A) The reaction zone A reactor from 1. at an external wall temperature along the heating zone of 500° C. under closed loop control (based on a tube flowed through by an identical inert gas stream) is charged with a reaction gas mixture of 20 l/h (STP) of isobutane, 10 l/h (STP) of air and 8 g/h of steam.

The isobutane is metered in using a mass flow regulator from Brooks, while the water is first metered into an evaporator using an HPLC pump 420 from Kontron, evaporated in it and then mixed with the isobutane and the air. During the charging, the temperature of the charging gas mixture is 150° C. The starting pressure in the tube reactor is set to 1.5 bar by means of a pressure regulator from REKO disposed at the reactor exit.

Downstream of the pressure regulator, the product gas mixture A is depressurized to atmospheric pressure and cooled, and the steam contained therein condenses out. The gas remaining is analyzed by means of GC (HP 6890 with Chem.-Station, detectors: FID; TCD, separating columns: $Al_2O_3/KCl$ (Chrompack), Carboxen 1010 (Supelco)). In a corresponding manner, the charging gas mixture is also analyzed.

After an operating time of three weeks, the following analytical results are obtained:

|  | Charging gas mixture (% by volume) | Product gas mixture A (% by volume) |
|---|---|---|
| isobutane | 50 | 33 |
| isobutene | — | 10 |
| Nitrogen | 20 | 17.5 |
| Steam | 25 | 26 |
| Oxygen | 5 | — |
| CO | — | <0.1 |
| $CO_2$ | — | 2.5 |
| $H_2$ | — | 11 |
| Propene | — | <0.1 |
| Propane | — | <0.1 |
| Ethene | — | <0.1 |
| Ethane | — | <0.1 |

These values correspond to an isobutane conversion based on a single pass of 25 mol % and a selectivity of isobutene formation of 90 mol %.

The portion of the reaction zone B reactor from 2. in the oven is maintained by closed loop control at an external wall temperature (based on a tube flowed through by an identical inert gas stream) at which the isobutene conversion at a single pass of the reaction mixture is 98 mol %. The heating band at the reaction tube entrance (where the catalyst base is disposed) is likewise set to this temperature and the heating band at the reaction tube exit is set to a temperature 50° C. lower. All components other than isobutane and isobutene are removed from the product gas mixture A.

The remaining mixture of 15 l/h (STP) of isobutane and 4.5 l/h (STP) of isobutene together with 45 l/h (STP) of air and 7 l/h (STP) of steam form the charging gas mixture for the reaction zone B reactor. The temperature of the charging gas mixture is increased to the reactor external wall temperature. The starting pressure in the reactor is set to 1.3 bar by means of a pressure regulator disposed at the reactor exit.

Downstream of the pressure regulator, the product gas mixture B (temperature =300° C.) is depressurized and analyzed by means of GC (HP 6890 with Chem.-Station, detectors: TCD, FID, separating columns: Poraplot Q (Chrompack), Carboxen 1010 (Supelco)). In an identical manner, the charging gas mixture is also analyzed.

After an operating time of 3 weeks, the following results are obtained:

|  | Charging gas mixture (% by volume) | Product gas mixture B (Vol.-%) |
|---|---|---|
| isobutane | 21 | 20.5 |
| isobutene | 6.5 | <0.1 |
| $H_2$ | — | — |
| $O_2$ | 12.5 | 3 |
| $N_2$ | 50 | 49 |
| $H_2O$ | 10 | 19 |
| Methacrolein | — | 5.2 |
| Methacrylic acid | — | <0.1 |

These values correspond to an isobutene conversion based on single pass of 98 mol % and a selectivity of methacrolein formation of 84 mol %.

The portion of the reaction C reactor in the furnace is maintained by closed loop control at an external wall temperature of 290° C. (based on a tube flowed through by an identical inert gas stream).

The heating band at the reaction tube entrance (where the catalyst base is disposed) is set to 290° C. and the heating band at the reaction tube exit is set to 200° C.

The charging gas mixture of the reaction zone C reactor consists of 29 l/h (STP) of air and the product gas mixture B (73 l/h (STP)). The temperature of the charging gas is increased to 290° C.

The pressure at the reaction tube exit is set to 1.3 bar using a pressure regulator disposed at the reactor exit.

Downstream of the pressure regulator, the product gas mixture C (temperature: 200° C.) is depressurized and analyzed by means of GC (HP 6890 with Chem.-Station, detectors: TCD, FID, separating columns: Poraplot Q (Chrompack), Carboxen 1010 (Supelco)). In a corresponding manner, the charging gas mixture is also analyzed.

After an operating time of 3 weeks, the following results are obtained:

|  | Charging gas mixture (% by volume) | Product gas mixture C (% by volume) |
|---|---|---|
| $N_2$ | 58 | 58 |
| $O_2$ | 8 | 6 |
| $H_2O$ | 14 | 14 |
| Methacrolein | 3.5 | 1.4 |
| Methacrylic acid | <0.1 | 1.7 |

These values correspond to a methacrolein conversion based on single pass of 60 mol % and a selectivity of methacrylic acid formation of 81 mol %.

5. Comparative Examples

A) The process according to the invention according to 4. is repeated. However, when the reaction zone B reactor is charged, the charging gas mixture used is a mixture of the entire product gas mixture A (41 l/h (STP) of which a proportion of 11 l/h (STP) is steam) and 45 l/h (STP) of air.

The loading of the catalyst charge in the reaction zone B reactor with isobutene and oxygen is accordingly 4.5 l/h (STP) of isobutene and 9 l/h (STP) of oxygen as in 4. and the loading of the catalyst charge in the reaction zone C reactor with methacrolein and oxygen is 3.8 l/h (STP) of methacrolein and 8 l/h (STP) of oxygen as in 4.

After an operating time of 3 weeks, the following results are obtained:

|  | Charging gas mixture (% by volume) | Product gas mixture C (% by volume) |
|---|---|---|
| $N_2$ | 55 | 55 |
| $O_2$ | 6.5 | 4.5 |
| $H_2O$ | 15 | 15.5 |
| Methacrolein | 3 | 1.8 |
| Methacrylic acid | <0.1 | 0.9 |

These values correspond to a methacrolein conversion based on single pass of 40 mol % and a selectivity of methacrylic acid formation of 75 mol %.

B) The process according to the invention according to 4. is repeated, except that instead of 45 l/h (STP) of air, 9 l/h (STP) of pure molecular oxygen are used for the charging gas for the reaction zone B reactor. The total isobutyraldehyde+isobutyric acid content of the product gas mixture C is perceptibly increased compared to the experimental procedure in 4.

We claim:

1. A process for preparing methacrylic acid from isobutane comprising
   A) subjecting isobutane in a reaction zone A to a partial heterogeneously catalyzed dehydrogenation in the gas phase to form a product mixture A which comprises isobutene and unconverted isobutane,
   B) charging a reaction zone B with the product gas mixture A and subjecting the isobutene in reaction zone B to a heterogeneously catalyzed partial oxidation in the gas phase with molecular oxygen to form a product gas mixture B comprising methacrolein, wherein the molar conversion of isobutene is ≧95 mol% and
   C) charging a reaction zone C with the product gas mixture B without prior removal of components contained therein and subjecting the methacrolein in a reaction zone C to a heterogeneously catalyzed partial oxidation with molecular oxygen in the gas phase to form a product gas mixture C comprising methacrylic acid,
   wherein at least 80 mol% of the components other than isobutane and isobutene in the product gas mixture A are removed before the charging to reaction zone B, and wherein the molecular oxygen is introduced to reaction zone B as a mixture with molecular nitrogen in a molar ratio R of molecular oxygen to molecular nitrogen of from 1:1 to 1:10.

2. The process as claimed in claim 1, wherein R is from 1:3 to 1:10.

3. The process as claimed in claim 1, wherein R is from 1:3 to 1:6.

4. The process as claimed in claim 1, wherein in zone B the molecular oxygen comprises air.

5. The process as claimed in claim 1, wherein at least 90 mol% of the components other than isobutane and isobutene present in the product gas mixture A are removed before the charging to reaction zone B.

6. The process as claimed in claim 1, wherein at least 95 mol% of the components other than isobutane and isobutene present in the product gas mixture A are removed before the charging to reaction zone B.

7. The process as claimed in claim 1, wherein in reaction zone A from $\geq 5$ mol% to $\leq 30$ mol% of isobutane is converted to isobutene.

8. The process as claimed in claim 1, further comprising
  contacting the product gas mixture A with an organic solvent to absorb isobutane and isobutene, and freeing the isobutane and isobutene from the organic solvent by subsequently desorbing, stripping or both, and charging the freed isobutene and isobutane to reaction zone B.

9. The process as claimed in claim 1, wherein at least 97 mol% of the isobutene is oxidized in the reaction zone B.

10. The process as claimed in claim 1, wherein at least 98 mol% of the isobutene is oxidized in reaction zone B.

11. The process as claimed in claim 1, further comprising
  supplementing the product gas mixture B with air before charging to reaction zone C.

* * * * *